United States Patent
Shang et al.

(10) Patent No.: US 11,583,580 B2
(45) Date of Patent: Feb. 21, 2023

(54) HEAT-RESISTANT H1N1 SUBTYPE INFLUENZA VIRUS MUTANT STRAIN, PREPARATION METHOD AND APPLICATION THEREOF

(71) Applicant: INSTITUTE OF ANIMAL HUSBANDRY AND VETERINARY SCIENCES, HUBEI ACADEMY OF AGRICULTURAL SCIENCES, Wuhan (CN)

(72) Inventors: Yu Shang, Wuhan (CN); Guoyuan Wen, Wuhan (CN); Li Li, Wuhan (CN); Huabin Shao, Wuhan (CN); Qingping Luo, Wuhan (CN); Honglin Wang, Wuhan (CN); Ling Luo, Wuhan (CN); Rongrong Zhang, Wuhan (CN); Hongcai Wang, Wuhan (CN); Tengfei Zhang, Wuhan (CN); Wenting Zhang, Wuhan (CN); Qin Lu, Wuhan (CN)

(73) Assignee: INSTITUTE OF ANIMAL HUSBANDRY AND VETERINARY SCIENCES, HUBEI ACADEMY OF AGRICULTURAL SCIENCES, Wuhan (CN)

( * ) Notice: Subject to any disclaimer, the term of this patent is extended or adjusted under 35 U.S.C. 154(b) by 24 days.

(21) Appl. No.: 17/234,785

(22) Filed: Apr. 19, 2021

(65) Prior Publication Data
US 2022/0096621 A1   Mar. 31, 2022

(30) Foreign Application Priority Data

Sep. 27, 2020 (CN) .......................... 202011035087.8

(51) Int. Cl.
| | | |
|---|---|---|
| A61K 39/145 | (2006.01) | |
| C12N 7/00 | (2006.01) | |
| A61K 39/00 | (2006.01) | |

(52) U.S. Cl.
CPC .............. *A61K 39/145* (2013.01); *C12N 7/00* (2013.01); *A61K 2039/525* (2013.01); *C12N 2760/16121* (2013.01); *C12N 2760/16152* (2013.01)

(58) Field of Classification Search
None
See application file for complete search history.

(56) References Cited

PUBLICATIONS

Klein et al., Stability of the Influenza Virus Hemagglutinin Protein Correlates with Evolutionary Dynamics, 2018, mSphere, vol. 3, No. 1, pp. 1-13.*

* cited by examiner

*Primary Examiner* — Benjamin P Blumel

(57) ABSTRACT

A heat-resistant H1N1 subtype influenza virus mutant strain rPR8-HA-N5 has been preserved at China Center for Type Culture Collection, Wuhan University, Wuhan, China with the preservation number of CCTCC No. V202043.

2 Claims, 2 Drawing Sheets

Specification includes a Sequence Listing.

SEQUENCE LISTING

```
<160> NUMBER OF SEQ ID NOS: 9

<210> SEQ ID NO 1
<211> LENGTH: 1698
<212> TYPE: DNA
<213> ORGANISM: Influenza Virus

<400> SEQUENCE: 1
atggaggcaa acctactggt cctgttaagt gcacttgcag ctgcagatgc agacacaata      60
tgtataggct accatgcgaa caattcaacc gacactgttg acacagtact cgagaagaat     120
gtgacagtga cacactctgt taacctgctc gaagacagcc acaacggaaa actatgtaga     180
ttaaaaggaa tagccccact acaattgggg aaatgtaaca tcgccggatg gctcttggga     240
aacccagaat gcgacccact gcttccagtg agttcatggt cctacattgt agaaacacca     300
aactctgaga tggaatatg ttatccagga gatttcatcg actatgagga gctgagggag     360
caattgagct cagtgtcatc attcgaaaga ttcgaaatat ttcccaaaga aagctcatgg     420
cccaaccaca acacaaacgg agtaacggca gcatgctccc atgagggggc aagcagtttt     480
tacagaaatt tgctatggct gacggagaag gagggctcat acccaaagct gaaaaattct     540
tatgtgaaca aaaaagggaa agaagtcctt gtactgtggg gtattcatca cccgcctaac     600
agtaaggaac aacagaatat ctatcagaat gaaaatgctt atgtctctgt agtgacttca     660
aattataaca ggagatttac cccggaaata gcagaaagac ccaaagtaag agatcaagct     720
gggaggatga actattactg gaccttgcta gaacccggag acacaataat atttgaggca     780
aatggaaatc taatagcacc aatgtatgct ttcgcactga gtagaggctt tgggtccggc     840
```

| | |
|---|---:|
| atcatcacct caaacgcatc aatgcatgag tgtaacacga agtgtcaaac acccctggga | 900 |
| gctataaaca gcagtctccc ttaccagaat atacacccag tcacaatagg agagtgccca | 960 |
| aaatacgtca ggagtgccaa attgaggatg gttacaggac taaggaacac tccgtccatt | 1020 |
| caatccagag gtctatttgg agccattgcc ggttttattg aaggggatg gactggaatg | 1080 |
| atagatggat ggtatggtta tcatcatcag aatgaacagg gatcaggcta tgcagcggat | 1140 |
| caaaaagca cacaaaatgc cattaacggg attacaaaca aggtgaacac tgttatcgag | 1200 |
| aaaatgaaca ttcaattcac agctgtgggt aaagaattca acaaattaga aaaaggatg | 1260 |
| gaaaatttaa ataaaaaagt tgatgatgga tttctggaca tttggacata taatgcagaa | 1320 |
| ttgttagttc tactggaaaa tgaaaggact ctggatttcc atgactcaaa tgtgaagaat | 1380 |
| ctgtatgaga agtaaaaag ccaattaaag aataatgcca agaaatcgg aaatggatgt | 1440 |
| tttgagttct accacaagtg tgacaatgaa tgcatggaaa gtgtaagaaa tgggacttat | 1500 |
| gattatccca atattcaga agagtcaaag ttgaacaggg aagaggtaga tggagtgaaa | 1560 |
| ttggaatcaa tggggatcta tcagattctg gcgatctact caactgtcgc cagttcactg | 1620 |
| gtgcttttgg tctccctggg ggcaatcagt ttctggatgt gttctaatgg atctttgcag | 1680 |
| tgcagaatat gcatctga | 1698 |

<210> SEQ ID NO 2
<211> LENGTH: 1778
<212> TYPE: DNA
<213> ORGANISM: Influenza Virus

<400> SEQUENCE: 2

| | |
|---|---:|
| agcaaaagca gggaaaata aaacaacca aaatgaaggc aaacctactg gtcctgttat | 60 |
| gtgcacttgc agctgcagat gcagacacaa tatgtatagg ctaccatgcg aacaattcaa | 120 |
| ccgacactgt tgacacagta ctagagaaga atgtgacagt gacacactct gttaacctgc | 180 |
| tcgaagacag ccacaacgga aaactatgta gattaaaagg aataaccca ctacaattgg | 240 |
| ggaattgtaa catcgccgga tggctcttgg gaaacccaga atgcgaccca ctgcttccag | 300 |
| tgagatcatg gtcctacatt gtagaaacac caaactctga gatggaata tgttatccag | 360 |
| gagatttcat cgactatgaa gaactgaggg agcaattgag ctcagtgtca tcattcgaaa | 420 |
| gattcgaaat atttcccaaa gaaagctcat ggcccaacca acacaaaac aaaggagtaa | 480 |
| cggcagcatg ctcccatgcg gggaaaagca gttttacag aaatttgcta tggctgacgg | 540 |
| agaaggaggg ctcatacca aagctgaaaa attcttatgt gaacaagaaa gggaaggaag | 600 |
| tccttgtact gtggggtatt catcacccgt ctaacagtaa ggaacaacag aatctctatc | 660 |
| agaatgaaaa tgcttatgtc tctgtagtga cttcaaatta aacaggaga tttaccccgg | 720 |
| aaatagcaga aagacccaaa gtaagagatc aagctgggag gatgaactat tactggacct | 780 |
| tgctaaaacc cggagacaca ataatatttg aggcaaatgg aaatctaata gcaccaaggt | 840 |
| atgctttcgc actgagtaga ggctttgggt ccggcatcat cacctcaaac gcatcaatgc | 900 |
| atgagtgtaa cacgaagtgt caaacacccc tgggagctat aaacagcagt ctccctttcc | 960 |
| agaatataca cccagtcaca ataggagagt gcccaaaata cgtcaggagt gccaaattga | 1020 |
| ggatggttac aggactaagg aacattccgt ccattcaatc cagaggtcta tttggagcca | 1080 |
| ttgccggttt tattgaaggt ggatggactg gaatgataga tggatggtat ggttatcatc | 1140 |
| atcagaatga acagggatca ggctatgcag cggatcaaaa aagcacacaa aatgccatta | 1200 |
| acgggattac aaacaaggtg aactctgtta tcgagaaaat gaacactcaa ttcacagctg | 1260 |

| | |
|---|---:|
| tgggtaaaga attcaacaaa ttagaaaaaa ggatggaaaa tttaaataaa aaagttgatg | 1320 |
| atggatttct ggacatttgg acatataatg cagaattgtt agttctactg gaaaatgaaa | 1380 |
| ggactctgga tttccatgac tcaaatgtga agaatctgta tgagaaagta aaaagccaat | 1440 |
| taaagaataa tgccaaagaa atcggaaatg gatgttttga gttctaccac aagtgtgaca | 1500 |
| atgaatgcat ggaaagtgta agaaatggga cttatgatta tcccaaatat tcagaagagt | 1560 |
| caaagttgaa cagggaaaag gtagatggag tgaaattgga atcaatgggg atctatcaga | 1620 |
| ttctggcgat ctactcaact gtcgccagtt cactggtgct tttggtctcc ctggggggcaa | 1680 |
| tcagtttctg gatgtgttct aatggatctt tgcagtgcag aatatgcatc tgagattaga | 1740 |
| atttcagaaa tatgaggaaa acacccttg tttctact | 1778 |

```
<210> SEQ ID NO 3
<211> LENGTH: 2341
<212> TYPE: DNA
<213> ORGANISM: Influenza Virus

<400> SEQUENCE: 3
```

| | |
|---|---:|
| agcaaaagca ggtcaattat attcaatatg gaaagaataa agaactaag aaatctaatg | 60 |
| tcgcagtctc gcacccgcga gatactcaca aaaaccaccg tggaccatat ggccataatc | 120 |
| aagaagtaca catcaggaag acaggagaag aacccagcac ttaggatgaa atggatgatg | 180 |
| gcaatgaaat atccaattac agcagacaag aggataacgg aaatgattcc tgagagaaat | 240 |
| gagcaaggac aaactttatg gagtaaaatg aatgatgccg gatcagaccg aatgatggta | 300 |
| tcacctctgg ctgtgacatg gtggaatagg aatggaccaa tgacaaatac agttcattat | 360 |
| ccaaaaatct acaaaactta ttttgaaaga gtcgaaaggc taaagcatgg aaccttttggc | 420 |
| cctgtccatt ttagaaacca agtcaaaata cgtcggagag ttgacataaa tcctggtcat | 480 |
| gcagatctca gtgccaagga ggcacaggat gtaatcatgg aagttgtttt ccctaacgaa | 540 |
| gtgggagcca ggatactaac atcggaatcg caactaacga taaccaaaga gaagaaagaa | 600 |
| gaactccagg attgcaaaat ttctccttta atggttgcat acatgttgga gagaactg | 660 |
| gtccgcaaaa cgagattcct cccagtggct ggtggaacaa gcagtgtgta cattgaagtg | 720 |
| ttgcatttga ctcaaggaac atgctgggaa cagatgtata ctccaggagg gaagtgagg | 780 |
| aatgatgatg ttgatcaaag cttgattatt gctgctagga acatagtgag aagagctgca | 840 |
| gtatcagcag atccactagc atctttattg gagatgtgcc acagcacaca gattggtgga | 900 |
| attaggatgt agacatcct taggcagaac ccaacagaag agcaagccgt ggatatatgc | 960 |
| aaggctgcaa tgggactgag aattagctca tccttcagtt ttggtggatt cacatttaag | 1020 |
| agaacaagcg atcatcagt caagagagag gaagaggtgc ttacgggcaa tcttcaaaca | 1080 |
| ttgaagataa gagtgcatga gggatatgaa gagttcacaa tggttgggag aagagcaaca | 1140 |
| gccatactca gaaaagcaac caggagattg attcagctga tagtgagtgg gagagacgaa | 1200 |
| cagtcgattg ccgaagcaat aattgtggcc atggtatttt cacaggagga ttgtatgata | 1260 |
| aaagcagtta gaggtgatct gaatttcgtc aataggcga atcagcgatt gaatcctatg | 1320 |
| catcaacttt taagacattt tcagaaggat gcgaaagtgc ttttttcagaa ttggggagtt | 1380 |
| gaacctatcg acaatgtgat gggaatgatt gggatattgc ccgacatgac tccaagcatc | 1440 |
| gagatgtcaa tgagaggagt gagaatcagc aaaaatgggt gtagatgagta ctccagcacg | 1500 |
| gagagggtag tggtgagcat tgaccggttt ttgagaatcc gggaccaacg aggaaatgta | 1560 |

| | |
|---|---|
| ctactgtctc ccgaggaggt cagtgaaaca cagggaacag agaaactgac aataacttac | 1620 |
| tcatcgtcaa tgatgtggga gattaatggt cctgaatcag tgttggtcaa tacctatcaa | 1680 |
| tggatcatca gaaactggga aactgttaaa attcagtggt cccagaaccc tacaatgcta | 1740 |
| tacaataaaa tggaatttga accatttcag tctttagtac ctaaggccat tagaggccaa | 1800 |
| tacagtgggt ttgtaagaac tctgttccaa caaatgaggg atgtgcttgg acatttgat | 1860 |
| accgcacaga taataaaact tcttcccttc gcagccgctc caccaaagca agtagaatg | 1920 |
| cagttctcct catttactgt gaatgtgagg ggatcaggaa tgagaatact tgtaagggc | 1980 |
| aattctcctg tattcaacta caacaaggcc acgaagagac tcacagttct cggaaaggat | 2040 |
| gctggcactt taactgaaga cccagatgaa ggcacagctg gagtggaatc cgctgttctg | 2100 |
| aggggattcc tcattctggg caagaagac aggagatatg gccagcatt aagcatcaat | 2160 |
| gaactgagca accttgcgaa aggagagaag gctaatgtgc taattgggca aggagacgtg | 2220 |
| gtgttggtaa tgaaacgaaa acgggactct agcatactta ctgacagcca gacagcgacc | 2280 |
| aaaagaattc ggatggccat caattagtgt cgaatagttt aaaaacgacc ttgtttctac | 2340 |
| t | 2341 |

<210> SEQ ID NO 4
<211> LENGTH: 2341
<212> TYPE: DNA
<213> ORGANISM: Influenza Virus

<400> SEQUENCE: 4

| | |
|---|---|
| agcgaaagca ggcaaaccat ttgaatggat gtcaatccga ccttactttt cttaaaagtg | 60 |
| ccagcacaaa atgctataag cacaactttc ccttataccg agaccctcc ctacagccat | 120 |
| gggacaggaa caggatacac catggatact gtcaacagga cacatcagta ctcagaaaag | 180 |
| ggaagatgga caacaaacac cgaaactgga gcaccgcaac tcaacccgat tgatgggcca | 240 |
| ctgccagaag acaatgaacc aagtggttat gcccaaacag attgtgtatt ggaagcaatg | 300 |
| gctttccttg aggaatccca tcctggtatt tttgaaaact cgtgtattga acgatggag | 360 |
| gttgttcagc aaaacacgagt agacaggctg acacaaggcc gacagaccta tgactggact | 420 |
| ctaaatagaa accagcctgc tgcaacagca ttggccaaca caatagaagt gttcagatca | 480 |
| aatggcctca cggccaatga gtctggaagg ctcatagact tccttaagga tgtaatggag | 540 |
| tcaatgaaca agaagaaat ggggatcaca actcattttc agagaaagag acgggtgaga | 600 |
| gacaatatga ctaagaaaat gataacacag agaacaatag gtaaaaggaa gcagagattg | 660 |
| aacaaaagga gttatctaat tagagcattg accctgaaca caatgaccaa agatgctgag | 720 |
| agagggaagc taaaacggag agcaattgca acccccaggga tgcaaataag ggggtttgta | 780 |
| tactttgttg agacactggc aagaagtata tgtgagaaac ttgaacaatc agggttgcca | 840 |
| gttggaggca atgagaagaa agcaaagttg gcaaatgttg taaggaagat gatgaccaat | 900 |
| tctcaggaca ccgaactttc tttcaccatc actggagata acaccaaatg aacgaaaat | 960 |
| cagaatcctc ggatgttttt ggccatgatc acatatatga ccagaaatca gcccgaatgg | 1020 |
| ttcagaaatg ttctaagtat tgctccaata atgttctcaa acaaaatggc gagactggga | 1080 |
| aagggtata tgtttgagag caagagtatg aaacttagaa cccaaatacc tgcagaaatg | 1140 |
| ctagcaagca ttgatttgaa atatttcaat gattcaacaa gaagaagat tgaaaaaatc | 1200 |
| cgaccgctct aatagagggg gactgcatca ttgagccctg aatgatgat gggcatgttc | 1260 |
| aatatgttaa gcactgtatt aggcgtctcc atcctgaatc ttggacaaaa gagatacacc | 1320 |

-continued

```
aagactactt actggtggga tggtcttcaa tcctctgacg attttgctct gattgtgaat    1380
gcacccaatc atgaagggat tcaagccgga gtcgacaggt tttatcgaac ctgtaagcta    1440
cttggaatca atatgagcaa gaaaaagtct tacataaaca gaacaggtac atttgaattc    1500
acaagttttt tctatcgtta tgggtttgtt gccaatttca gcatggagct tcccagtttt    1560
ggggtgtctg ggatcaacga gtcagcggac atgagtattg agttactgt catcaaaaac     1620 aatatgataa acaatgatct tggtccagca acagctcaaa tggcccttca gttgttcatc    1680
aaagattaca ggtacacgta ccgatgccat agaggtgaca cacaaataca aacccgaaga    1740
tcatttgaaa taaagaaact gtgggagcaa acccgttcca aagctggact gctggtctcc    1800
gacggaggcc caaatttata caacattaga aatctccaca ttcctgaagt ctgcctaaaa    1860
tgggaattga tggatgagga ttaccagggg cgtttatgca acccactgaa cccatttgtc    1920
agccataaag aaattgaatc aatgaacaat gcagtgatga tgccagcaca tggtccagcc    1980
aaaaacatgg agtatgatgc tgttgcaaca acacactcct ggatccccaa agaaatcga    2040 tccatcttga atacaagtca agaggagta cttgaagatg aacaaatgta ccaaaggtgc     2100
tgcaatttat ttgaaaaatt cttccccagc agttcataca aagaccagt cgggatatcc     2160 agtatggtgg aggctatggt ttccagagcc cgaattgatg cacggattga tttcgaatct    2220
ggaaggataa agaagaaga gttcactgag atcatgaaga tctgttccac cattgaagag    2280
ctcagacggc aaaaatagtg aatttagctt gtccttcatg aaaaaatgcc ttgtttctac     2340
t                                                                    2341
```

<210> SEQ ID NO 5
<211> LENGTH: 2233
<212> TYPE: DNA
<213> ORGANISM: Influenza Virus

<400> SEQUENCE: 5

```
agcgaaagca ggtactgatc caaaatggaa gattttgtgc gacaatgctt caatccgatg     60
attgtcgagc ttgcggaaaa aacaatgaaa gagtatgggg aggacctgaa atcgaaaca    120 aacaaatttg cagcaatatg cactcacttg gaagtatgct tcatgtattc agattttcac    180
ttcatcaatg agcaaggcga gtcaataatc gtagaacttg gtgatccaaa tgcacttttg    240
aagcacagat ttgaaataat cgagggaaga gatcgcacaa tggcctggac agtagtaaac    300
agtatttgca acactacagg ggctgggaaa ccaaagtttc taccagattt gtatgattac    360
aaggagaata gattcatcga aattggagta acaaggagaa agttcacat atactatctg    420 gaaaaggcca ataaaattaa atctgagaaa acacacatcc acatttctc gttcactggg    480 gaagaaatgg ccacaaaggc agactacact ctcgatgaag aaagcagggc taggatcaaa    540
accagactat tcaccataag acaagaaatg gccagcagag gcctctggga ttcctttcgt    600
cagtccgaga gaggagaaga gacaattgaa gaaaggtttg aaatcacagg aacaatgcgc    660
aagcttgccg accaaagtct cccgccgaac ttctccagcc ttgaaaattt tagagcctat    720
gtggatggat tcgaaccgaa cggctacatt gagggcaagc tgtcccaaat gtccaaagaa    780
gtaaatgcta gaatcgaacc ttttttgaaa acaacaccac gaccacttag acttccgaat    840 gggcctcct gttctcagcg gtccaagttc ctgctgatgg atgccttaaa attaagcatt    900
gaggacccaa gtcatgaagg agagggaata ccgctatatg atgcaatcaa atgcatgaga    960
acattctttg gatggaagga acccaatgtt gttaaaccac acgaaaaggg aataaatcca    1020
```

-continued

```
aattatcttc tgtcatggaa gcaagtactg gcagaactgc aggacattga gaatgaggag    1080
aaaattccaa agactaaaaa tatgaagaaa acaagtcagc taaagtgggc acttggtgag    1140
aacatggcac cagaaaaggt agactttgac gactgtaaag atgtaggtga tttgaagcaa    1200
tatgatagtg atgaaccaga attgaggtcg cttgcaagtt ggattcagaa tgagtttaac    1260
aaggcatgcg aactgacaga ttcaagctgg atagagctcg atgagattgg agaagatgtg    1320
gctccaattg aacacattgc aagcatgaga aggaattatt tcacatcaga ggtgtctcac    1380
tgcagagcca cagaatacat aatgaagggg gtgtacatca atactgcctt gcttaatgca    1440
tcttgtgcag caatggatga tttccaatta attccaatga taagcaagtg tagaactaag    1500
gagggaaggc gaaagaccaa cttgtatggt ttcatcataa aaggaagatc ccacttaagg    1560
aatgacaccg acgtggtaaa ctttgtgagc atggagtttt ctctcactga cccaagactt    1620
gaaccacaca aatgggagaa gtactgtgtt cttgagatag agatatgct tctaagaagt    1680 gccataggcc aggtttcaag gcccatgttc ttgtatgtga aacaaatgg aacctcaaaa    1740 attaaaatga atggggaat ggagatgagg cgttgcctcc tccagtcact tcaacaaatt    1800
gagagtatga ttgaagctga gtcctctgtc aaagagaaag acatgaccaa agagttcttt    1860
gagaacaaat cagaaacatg gcccattgga gagtccccca aaggagtgga ggaaagttcc    1920
attgggaagg tctgcaggac tttattagca aagtcggtat tcaacagctt gtatgcatct    1980
ccacaactag aaggattttc agctgaatca agaaaactgc ttcttatcgt tcaagctctt    2040
agggacaacc tggaacctgg gacctttgat cttggggggc tatatgaagc aattgaggag    2100
tgcctaatta atgatccctg ggttttgctt aatgcttctt ggttcaactc cttccttaca    2160
catgcattga gttagttgtg gcagtgctac tatttgctat ccatactgtc caaaaaagta    2220
ccttgtttct act                                                      2233
```

<210> SEQ ID NO 6
<211> LENGTH: 1413
<212> TYPE: DNA
<213> ORGANISM: Influenza Virus

<400> SEQUENCE: 6

```
agcgaaagca ggagtttaaa atgaatccaa atcagaaaat aataaccatt ggatcaatct     60
gtatggtagt cggactaatt aacctactat tgcaaatagg gaatataatc tcaatatgga    120
ttagccattc aattcaaact ggaagtcaaa accatactgg aatatgcaac caaaacatca    180
ttacctataa aaatagcacc tgggtaaagg acacaacttc agtgatatta accggcaatt    240
catctctttg tcccatccgt gggtgggcta tatacagcaa agacaatacc ataagaattg    300
gttccaaagg agacgttttt gtcataagag agcccttat ttcatgttct cacttggaat    360
gcaggacctt ttttctgacc caaggtgcct tactgaatga caagcattca aatgggactg    420
ttaaggacag aagcccttat agggccttaa tgagctgccc tgtcggtgaa gctccgtccc    480
cgtacaattc aagatttgaa tcggttgctt ggtcagcaag tgcatgtcat gacggcatgg    540
gctggctaac aatcggaatt tcaggtccag ataatggagc agtggctgta ttaaaataca    600
acggcataat aactgaaacc ataaaaagtt ggaggaagaa atattgagg acacaagagt    660 ctgaatgtgc ctgtgtaaat ggatcatgtt ttactataat gactgatggc ccgagtgatg    720
ggctggcctc gtacaaaatt ttcaagatcg aaaaggggaa ggttactaaa tcaatagagt    780
tgaatgcacg taatttttcac tacgaggaat gttcctgtta ccctgatacc ggcaaagtga    840
tgtgtgtgtg cagagacaat tggcatggtt cgaaccggcc atgggtgtct ttcgatcaaa    900
```

```
acctggatta tcaaatagga tacatctgca gtggggtttt cggtgacaat ccgcgtccca    960
aagatggaac aggcagctgt ggtccagtgt atgttgatgg agcaaacgga gtaaagggat   1020
tttcatatag gtatggtaat ggtgtttgga taggaaggac caaaagtcac agttccagac   1080
atgggtttga gatgatttgg gatcctaatg gatggacaga gactgatagt aagttctctg   1140
tgaggcaaga tgttgtggca atgactgatt ggtcagggta tagcggaagt ttcgttcaac   1200
atcctgagct aacagggcta gactgtataa ggccgtgctt ctgggttgaa ttaatcaggg   1260
gacgacctaa agaaaacaca atctggacta gtgcgagcag catttctttt tgtggcgtga   1320
atagtgatac tgtagattgg tcttggccag acggtgctga gttgccattc accattgaca   1380
agtagtctgt tcaaaaaact ccttgtttct act                                1413

<210> SEQ ID NO 7
<211> LENGTH: 1565
<212> TYPE: DNA
<213> ORGANISM: Influenza Virus

<400> SEQUENCE: 7
agcaaaagca gggtagataa tcactcactg agtgacatca aaatcatggc gtcccaaggc     60
accaaacggt cttacgaaca gatggagact gatggagaac gccagaatgc cactgaaatc    120
agagcatccg tcggaaaaat gattggtgga attggacgat tctacatcca aatgtgcacc    180
gaacttaaac tcagtgatta tgagggacgg ttgatccaaa acagcttaac aatagagaga    240
atggtgctct ctgcttttga cgaaaggaga aataaatacc tggaagaaca tcccagtgcg    300
gggaaagatc ctaagaaaac tggaggacct atatacagga gagtaaacgg aaagtggatg    360
agagaactca tcctttatga caagaagaa ataaggcgaa tctggcgcca agctaataat    420
ggtgacgatg caacggctgg tctgactcac atgatgatct ggcattccaa tttgaatgat    480
gcaacttatc agaggacaag agctcttgtt cgcaccggaa tggatccag atgtgctct    540 ctgatgcaag gttcaactct ccctaggagg tctggagccg caggtgctgc agtcaaagga    600
gttggaacaa tggtgatgga attggtcagg atgatcaaac gtgggatcaa tgatcggaac    660
ttctggaggg gtgagaatgg acgaaaaaca agaattgctt atgaaagaat gtgcaacatt    720
ctcaaaggga aatttcaaac tgctgcacaa aaagcaatga tggatcaagt gagagagagc    780
cggaacccag ggaatgctga gttcgaagat ctcacttttc tagcacggtc tgcactcata    840
ttgagagggt cggttgctca caagtcctgc ctgcctgcct gtgtgtatgg acctgccgta    900
gccagtgggt acgactttga agagaggga tactctctag tcggaataga ccctttcaga    960
ctgcttcaaa acagccaagt gtacagccta atcagaccaa atgagaatcc agcacacaag    1020
agtcaactgg tgtggatggc atgccattct gccgcatttg aagatctaag agtattaagc    1080
ttcatcaaag gacgaaggt ggtcccaaga gggaagcttt ccactagagg agttcaaatt    1140
gcttccaatg aaaatatgga gactatggaa tcaagtacac ttgaactgag aagcaggtac    1200
tgggccataa ggaccagaag tggaggaaac accaatcaac agagggcatc tgcgggccaa    1260
atcagcatac aacctacgtt ctcagtacag agaaatctcc cttttgacag aacaaccatt    1320
atggcagcat tcactgggaa tacagagggg agaacatctg acatgaggac cgaaatcata    1380
aggatgatgg aaagtgcaag accagaagat gtgtctttcc aggggcgggg agtcttcgag    1440
```

-continued

| | |
|---|---|
| ctctcggacg aaaaggcagc gagcccgatc gtgccttcct ttgacatgag taatgaagga | 1500 |
| tcttatttct tcggagacaa tgcagaggag tacgacaatt aaagaaaaat acccttgttt | 1560 |
| ctact | 1565 |

<210> SEQ ID NO 8
<211> LENGTH: 1369
<212> TYPE: DNA
<213> ORGANISM: Influenza Virus

<400> SEQUENCE: 8

| | |
|---|---|
| aggctagcag ttaccggagt actggtcgac ctccgaagtt ggggggggagc aaaagcaggt | 60 |
| agatattgaa agatgagtct tctaaccgag gtcgaaacgt acgttctctc tatcatcccg | 120 |
| tcaggccccc tcaaagccga gatagcacag agacttgaag atgtctttgc agggaagaac | 180 |
| accgatcttg aggttctcat ggaatggcta agacaagac caatcctgtc acctctgact | 240 |
| aaggggattt taggatttgt gttcacgctc accgtgccca gtgagcgagg actgcagcgt | 300 |
| agacgctttg tccaaactgc ccttaatggg aacggggatc caaataacat ggacaaagca | 360 |
| gttaaactgt ataggaagct caagaggag ataacattcc atggggccaa agaaatctca | 420 |
| ctcagttatt ctgctggtgc acttgccagt tgtatgggcc tcatatacaa caggatgggg | 480 |
| gctgtgacca ctgaagtggc atttggcctg gtatgtgcaa cctgtgaaca gattgctgac | 540 |
| tcccagcatc ggtctcatag caaatggtg acaacaacca atccactaat cagacatgag | 600 |
| aacagaatgg ttttagccag cactacagct aaggctatgg agcaaatggc tggatcgagt | 660 |
| gagcaagcag cagaggccat ggaggttgct agtcaggcta ggcaaatggt gcaagcgatg | 720 |
| agaaccattg ggactcatcc tagctccagt gctggtctga aaaatgatct tcttgaaaat | 780 |
| ttgcaggcct atcagaaacg aatggggtg cagatgcaac ggttcaagtg atcctctcgc | 840 |
| tattgccgca aatatcattg ggatcttgca cttgacattg tggattcttg atcgtctttt | 900 |
| tttcaaatgc atttaccgtc gctttaaata cggactgaaa ggagggcctt ctacggaagg | 960 |
| agtgccaaag tctatgaggg aagaatatcg aaaggaacag cagagtgctg tggatgctga | 1020 |
| cgatggtcat tttgtcagca tagagctgga gtaaaaaact accttgtttc tactaataac | 1080 |
| ccggcggccc aaaatgccga ctcggagcga aagatatacc tccccgggg ccggaggtc | 1140 |
| gcgtcaccga ccacgccgcc ggcccaggcg acgcgcgaca cggacacctg tcccaaaaa | 1200 |
| cgccaccatc gcagccacac acggagcgcc cggggccctc tggtcaaccc caggacacac | 1260 |
| gcgggagcag cgccgggccg gggacgcct cccggcggtc acctaaatgc tagagctcgc | 1320 |
| tgatcagcct cgactgtgcc ttctagtgcc agccatccgt gtcttctta | 1369 |

<210> SEQ ID NO 9
<211> LENGTH: 865
<212> TYPE: DNA
<213> ORGANISM: Influenza Virus

<400> SEQUENCE: 9

| | |
|---|---|
| gtgacaaaaa cataatggat tcaaacactg tgtcaagctt tcaggtagat tgctttctt | 60 |
| ggcatgtccg caagcgagtt gcagaccaag aactaggtga tgccccattc cttgatcggc | 120 |
| ttcgccgaga tcagaaatcc ctaagaggaa ggggcagcac tctcggtctg acatcgaga | 180 |
| cagccacacg tgctggaaag cagatagtgg agcggattct gaaagaagaa tccgatgagg | 240 |
| cacttaaaat gaccatggcc tctgtacctg cgtcgcgtta cctaactgac atgactcttg | 300 |

```
aggaaatgtc aagggactgg tccatgctca tacccaagca gaaagtggca ggccctcttt    360
gtatcagaat ggaccaggcg atcatggata agaacctcat actgaaagcg aacttcagtg    420 tgattttga ccggctggag actctaatat tgctaagggc tttcaccgaa gagggagcaa     480
ttgttggcga aatttcacca ttgccttctc ttccaggaca tactgctgag gatgtcaaaa    540
atgcagttgg agtcctcatc ggagggcttg aatggaatga taacacagtt cgagtctctg    600
aaactctaca gagattcgct tggagaagca gtaatgagaa tgggagacct ccactcactc    660
caaaacagaa acgagaaatg gcgggaacaa ttaggtcaga agtttgaaga aataagatgg    720
ttgattgaag aagtgagaca caaactgaag gtaacagaga atagttttga gcaaataaca    780
tttatgcaag ccttacatct attgcttgaa gtggagcaag agataagaac tttctcgttt    840
cagcttattt agtaataaaa aacac                                          865
```

HEAT-RESISTANT H1N1 SUBTYPE INFLUENZA VIRUS MUTANT STRAIN, PREPARATION METHOD AND APPLICATION THEREOF

TECHNICAL FIELD

The present disclosure relates molecular biology technology and microbiology. More specifically, the present disclosure relates to a heat-resistant H1N1 subtype influenza virus mutant strain and a preparation method and application thereof.

BACKGROUND

Influenza is a respiratory disease caused by the influenza virus and mainly infringes the respiratory system. It is widespread worldwide and seriously threatens the safety of public health and the healthy development of aquaculture. The influenza virus is a member of the genus Influenza virus of the Orthomyxoviridae family, which is a segmented negative-strand RNA, enveloped virus. The virus genome contains 8 gene segments: PB2, PB1, PA, HA, NP, NA, M and NS. Influenza viruses can be divided into four types: A, B, C and D according to the serotype. According to the structure and sequence characteristics of Hemagglutinin (HA) and Neuraminidase (NA), influenza A viruses can be divided into 18 HA subtypes and 11 NA subtypes. Because the RNA polymerase protein of influenza virus has a weaker ability to correct during the RNA synthesis process, the mutation frequency of the genome is higher, resulting in antigenic drift. In addition, the influenza genome is segmented. When influenza viruses of different subtypes infect the same cell, gene fragments will be recombined, triggering antigenic changes. The occurrence of these two conditions increases the difficulty of influenza prevention and control.

At present, there is no specific medicine for the influenza virus. There are several anti-influenza drugs that have the ability to inhibit the virus, but all have a certain degree of toxic side effects. Influenza vaccination is considered to be the most economical and effective way to prevent and control influenza epidemics. The World Health Organization (WHO) established an influenza surveillance system as early as 1947, through epidemiological investigations and monitoring data analysis, to predict the virus strains that will be circulating in the next influenza season, and make full preparations for development as early as possible. Commonly used influenza vaccines at home and abroad at this stage include: whole virus inactivated vaccines, split vaccines, subunit vaccines, and live attenuated vaccines. Vaccines under development include: DNA vaccines, mRNA vaccines, recombinant vector vaccines, virus-like particle vaccines, general vaccines, etc. Among them, the most widely used are whole virus inactivated vaccines and live attenuated vaccines. Inactivated vaccines are highly immunogenic, have a long immune protection period, and are less affected by maternal antibodies. Live attenuated vaccines can trigger better cellular immunity and produce faster immune responses. These vaccines have played an important role in influenza prevention and control.

The effective antigen component of the vaccine is the key to ensuring its immune effect. However, the thermal stability of existing vaccine strains is generally poor. Such vaccines require strict cryopreservation and cold chain transportation, and a large amount of additional costs are spent on vaccine storage and transportation every year. Even so, due to problems such as improper use and storage, the vaccine's immune efficacy is reduced, and even failures still occur. According to incomplete statistics, some types of vaccines were eventually abandoned due to poor thermal stability; nearly 50% of them will eventually be discarded. Therefore, improving the thermal stability of vaccine strains and developing heat-resistant vaccines is one of the important directions for the development of new vaccines.

Most reports on improving the thermal stability of influenza vaccines are by adding heat-resistant protective agents. For example, the patent application "An influenza virus subunit vaccine protective agent and application thereof" with the application number CN201510583080.2 discloses a vaccine protective agent with sucrose, arginine, sodium glutamate and genetically recombinant human albumin as the main components. The patent application "Avian influenza hemagglutinin antigen protective agent and method for improving the stability of avian influenza hemagglutinin in embryo fluid" with application number CN201210489259.8 discloses a vaccine protective agent composed of glycine, isoleucine, lactose and the like. The rapid development of reverse genetic manipulation technology makes it possible to perform genetic manipulations such as point mutation modification, insertion of foreign genes, and gene fragment exchange on influenza viruses. There are many literatures on the reverse genetic manipulation of influenza virus, but there are very few reports concerning the method of point mutation heat-resistant transformation of influenza virus.

DRAWING DESCRIPTION

FIG. 1 is a schematic diagram of gene structure of the influenza virus mutant strains.

FIG. 2 shows the results of HA thermo stability assays of the influenza virus mutant strains.

FIG. 3 is a cell proliferation curve of the influenza virus mutant strains.

FIG. 4 shows mouse pathogenicity results of the influenza virus mutant strains.

DETAILED DESCRIPTION

The present disclosure will be further described below with reference to the figures and examples, but the content of the present disclosure is not limited to the following examples.

Example 1

Figures 1, 2:
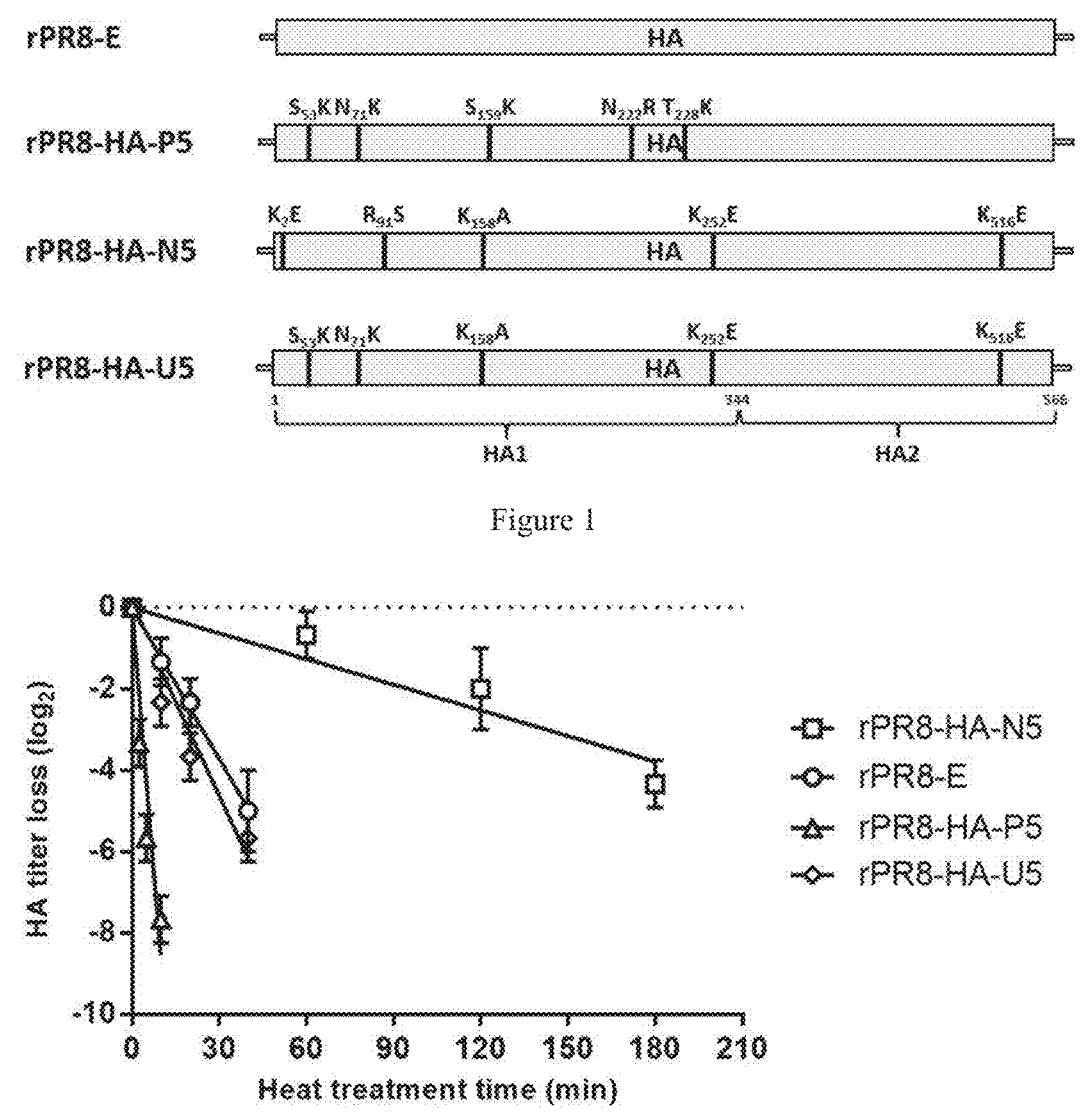

Construction of a Transcription Plasmid of HA Gene of H1N1 Subtype Influenza Virus Mutant Strain and Virus Rescue 1.1 Mutated HA Gene Sequence Three mutated HA gene sequences (HA-P5, HA-N5, HA-U5) were obtained by gene synthesis (FIG. 1). The mutation scheme of HA-P5 was that the S at position 53 was mutated to K, the N at position 71 was mutated to K, the S at position 159 was mutated to K, the N at position 222 was mutated to R and the T at position 228 was mutated to K. The mutation scheme of HA-N5 was that the K at position 2 was mutated to E, the R at position 91 was mutated to S, the K at position 158 was mutated to A, the K at position 252 was mutated to E, and the K at position 516 was mutated to E. The mutation scheme of HA-U5 was that the S at position 53 was mutated to K, the N at position 71 was mutated to K, the K at position 158 was mutated to A, the K at position 252 was mutated to E, and the K at position 516 was mutated to E. The synthesized genes were respectively connected to the cloning plasmid.

Using the cloned plasmid containing the synthetic gene as a template, high-fidelity DNA polymerase PrimeSTAR® GXL was used to amplify the mutated HA gene. The PCR products were detected by agarose gel electrophoresis and the specific target bands were recovered using a DNA gel recovery kit to obtain the mutated HA gene fragments.

1.2 Connection and Identification of the Mutated HA Gene Transcription Plasmid

A pair of PCR primers was designed and synthesized to amplify all sequences except the HA gene in the transcription plasmid of pPR8-HA. The pPR8-HA has the sequence of SEQ ID NO: 2. Through primer extension, part of the HA gene sequence was introduced at both ends of the PCR product, so that the PCR product and the mutated HA gene fragment can have a consistent sequence that can be used for homologous recombination. The target band was detected by agarose gel electrophoresis, and the PCR amplified band was purified and recovered with a DNA purification kit to obtain a fragment of HA gene transcription plasmid of the PR8-E strain (except HA gene).

According to the instruction of In-Fusion HD Cloning Kit, the mutated HA gene fragment and transcription plasmid (except HA gene) of HA gene of the PR8-E strain were ligated in-fusion, and transformed into DH5α competent cells. The resistant LB plates were coated with the cells, inverted cultured for 16 hours, and then a single colony was picked for PCR identification. Expand the culture of positive colonies and extract the plasmid, so the mutated HA gene transcription plasmid pPR8-HA-P5 (control group), PPR8-HA-N5 (present disclosure) and pPR8-HA-U5 (control group) were obtained.

1.3 Rescue of Mutant Virus

When 293T cells are cultured to 80-90% density, the mutated HA gene transcription plasmid and the remaining seven gene transcription plasmids of PR8-E strain pPR8-PB2 (listed as SEQ ID NO:3), pPR8-PB1 (listed as SEQ ID NO:4), pPR8-PA (listed as SEQ ID NO:5), pPR8-NA (listed as SEQ ID NO:6), pPR8-NP (listed as SEQ ID NO:7), PPR8-M (listed as SEQ ID NO:8) and pPR8-NS (listed as SEQ ID NO:9) co-transfected into 293T cells. After 5-6 hours of transfection, discard the supernatant and replace the maintenance solution (serum-free DMEM medium containing 1 µg/ml TPCK-treated trypsin). After 96-120 h, collect the culture supernatant, filter the culture supernatant with a 0.22 µm filter; then inoculate 9-10 day-old SPF chicken embryos, culture for 48-72 h, and collect allantoic fluid of viral chicken embryo. The point mutations of the virus in the allantoic fluid were verified by PCR and sequencing analysis and the results showed that the mutation sites of the mutant strains were consistent with expectations. Recombinant H1N1 influenza virus strains rPR8-HA-P5 (control group), rPR8-HA-N5 (present disclosure) and rPR8-HA-U5 (control group) with point mutations in the HA gene were obtained. The HA protein gene of the rPR8-HA-N5 has the sequence of SEQ ID NO: 1. The strain rPR8-HA-N5 is H1N1 subtype Avian influenza virus, belongs to genus influenza A virus in the family Orthomyxoviridae. The H1N1 influenza virus strain rPR8-HA-N5 has been preserved at the China Center for Type Culture Collection (CCTCC) with the preservation number of CCTCC No. V202043. The date of deposit is on Jul. 31, 2020. The address of the depository is: Wuhan university, Wuhan, China; Code: 430072.

Example 2

Thermal Stability Test of Recombinant H1N1 Influenza Virus Strain with Point Mutation of HA Gene The allantoic fluid infected with three mutant strains of Influenza virus with 100 µL/tube, was heat-treated in a 56° C. water bath. The virus allantoic fluid of the virus was take out at 0, 2, 5, 10, 15, 30, 60, 120, and 180 minutes, and quickly placed on ice to detect the HA titer of the virus and three replicates were set up. Statistics on the changes in titers are shown in FIG. 2. As shown in FIG. 2, The HA titer of rPR8-HA-P5 strain has decreased to 0 after heat treatment for 10 min. After heat treatment for 30 min, the HA titer of rPR8-HA-U5 has decreased by 5 $\log_2$, and after heat treatment for 180 min, it's HA titer has decreased by 4 $\log_2$. However, the HA titer of the control wild-type PR8-E strain decreased by 5 $\log_2$ after heat treatment for 30 min. Therefore, compared with the parent strain PR8-E, the three mutant viruses showed completely different HA thermal stability. The thermal stability of the rPR8-HA-N5 strain was significantly improved, and the thermal stability of the rPR8-HA-P5 strain was significantly decreased. The thermal stability of rPR8-HA-U5 has not changed significantly. Therefore, among the three mutant strains, only the rPR8-HA-N5 strain had a significant improvement in thermal stability, which was about six times higher than that of the parent strain PR8-E.

Example 3

Cell Proliferation Test of the Recombinant Influenza Virus rPR8-HA-N5 Strain

In order to analyze whether the point mutation affects the cell proliferation titer of the rPR8-HA-N5 strain, the cell proliferation of the rPR8-HA-N5 strain were compared with that of the parent strain PR8-E. The virus was propagated by chicken embryo inoculation, and both the rPR8-HA-N5 strain and PR8-E strain could reach more than $2^8$, and the half infection dose of chicken embryo was $10^{9.05}$ and $10^{8.90}$ $EID_{50}$/ml, respectively. The proliferation titers on the cells were $10^{7.78}$ and $10^{7.86}$ $TCID_{50}$/ml, respectively.

Figures 3, 4:
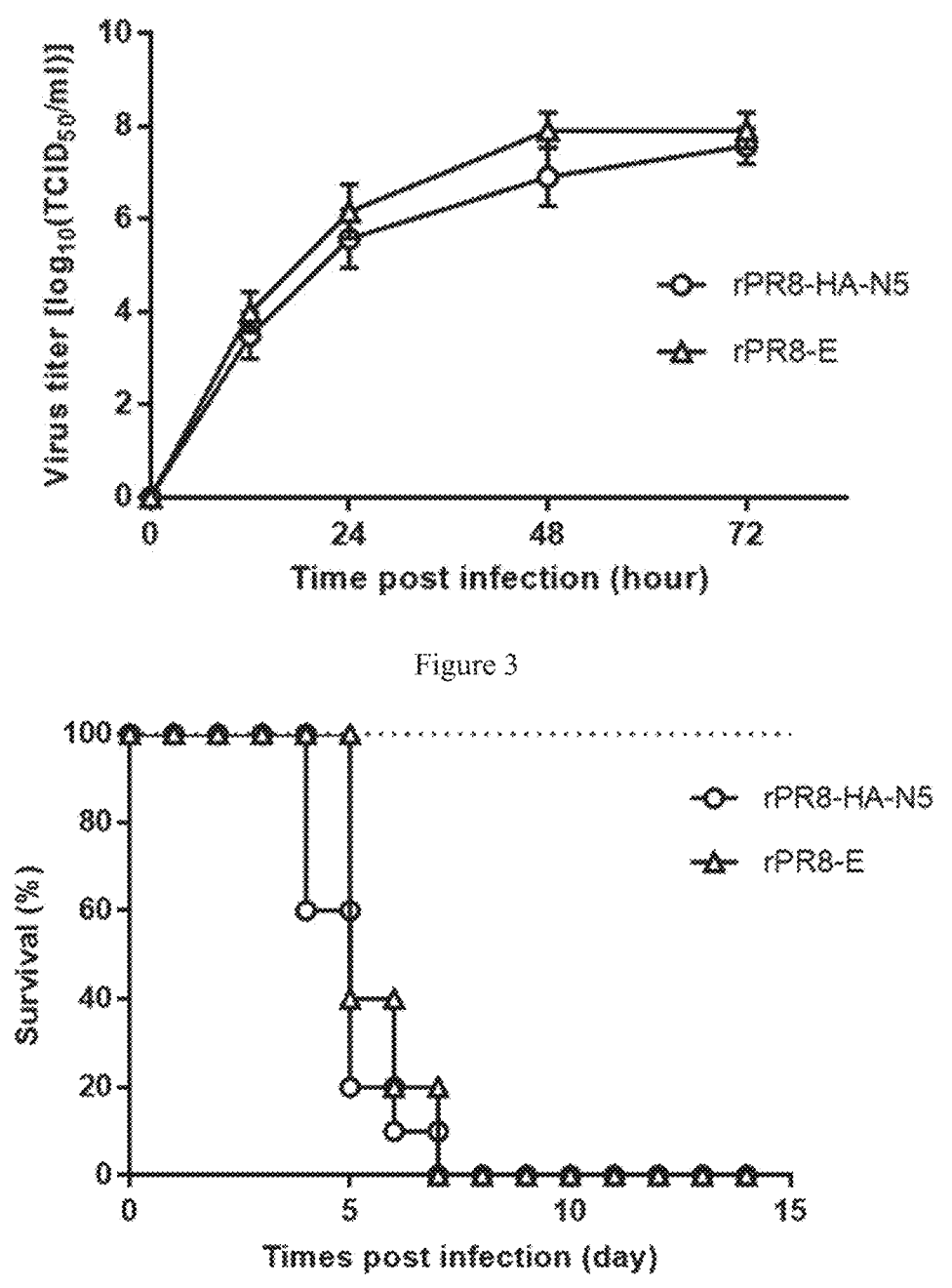

The cell growth curves of rPR8-HA-N5 and rPR8-E strains were further determined. The virus was inoculated into 293T cells that had grown into a dense monolayer at a dose of 0.002 MOI. After incubating for 1 hour, the supernatant was discarded and washed with PBS for 3 times. At 6, 12, 24, 48, and 72 hours after infection, the culture supernatant was sucked to determine the virus titer. The specific determination method was as follows: a 10-fold dilution of the virus solution from $10^{-1}$ to $10^{-8}$ was prepared, with 100 µl of each dilution added to a 96-well plate containing a single layer of 293T cells, and 5 replicates for each dilution. After 1 hour of infection, the culture medium was discarded, and the maintenance medium was added (serum-free DMEM medium containing 1 µg/ml TPCK-treated trypsin), and then was placed in a 37° C., 5% $CO_2$ incubator. Cytopathic change was observed after 72 h. The virus titer was calculated at each time point according to the number of cytopathic wells. According to the measured virus titer and the corresponding culture time point, the cell growth curve of the point mutation influenza virus was obtained. The results are shown in FIG. 3. The rPR8-HA-N5 and rPR8-E strains had similar growth curves, and there was no significant difference in the final titer. It showed that point mutations did not negatively affect the proliferation titer of rPR8-HA-N5.

Example 4

Pathogenicity Analysis of the Recombinant Influenza Virus rPR8-HA-N5 Strain

In order to analyze whether the point mutation affects the pathogenicity of the rPR8-HA-N5 strain, the pathogenicity of the rPR8-HA-N5 strain and the parent PR8-E strain in mice was determined. Four-week-old mice were divided into 3 groups, each with 20 mice, namely rPR8-HA-N5 group, rPR8-E group and blank control group. The infection method was intramuscular injection, and the infection dose was $10^{3.0}$ $EID_{50}$/mouse. The state of the mice was observed every day, the death was recorded, and the animal's survival curve was drawn. The results were shown in FIG. 4, 5-7 days after infection, all mice in the three groups died, indicating that the mutant strain rPR8-HA-N5 has similar pathogenicity to the parent strain of rPR8-E.

Example 5

Immunogenicity Analysis of the Recombinant Influenza Virus rPR8-HA-N5 Strain

In order to analyze whether the point mutation affects the immune prototype of rPR8-HA-N5, the immune effect test of rPR8-HA-N5 strain as an inactivated vaccine in mice was carried out. The allantoic fluid infected with rPR8-HA-N5 strain was inactivated with β-propiolactone, mixed with a certain immune adjuvant, and inoculated into mice (0.2 ml/mouse) by intramuscular injection. PR8-E strain control group and blank control group were set. The immunization was added once two weeks later, and blood was collected two weeks after the second immunization to determine the HI antibody level. The results showed that, except for the blank control group, the other two groups were positive for HI antibodies. The average antibody of the rPR8-HA-N5 strain was $2^{6.8}$, and that of the PR8-E group was $2^{6.1}$. Therefore, the immunogenicity of the rPR8-HA-N5 strain to mice is higher than that of the parent PR8-E strain, and can be used as a candidate strain for influenza heat-resistant vaccine.

The beneficial effects of the present disclosure are:

1) The amino acids at position 2, 91, 158, 252 and 516 of HA gene of the transcription plasmid are mutated to glutamic acid, serine, alanine, glutamic acid and glutamic acid, respectively based on the eight transcription plasmids of the H1N1 subtype influenza virus of non-heat-resistant strain PR8-E. The transcription plasmid with point mutations thus is constructed and new mutant strains is obtained through virus rescue. The results of the biological characteristics test showed that the heat-resistant characteristics of the mutant strain were significantly higher than that of the PR8-E parent strain, while other characteristics did not change significantly, confirming that a heat-resistant modified, new influenza mutation strain is obtained.

2) Compared with other influenza vaccine strains, the modified heat-resistant vaccine strain has a better thermal stability. The vaccine prepared can be stored and transported without excessively relying on low temperature and cold chain transportation equipment. And there is no need to add heat-resistant protective agents to extend the shelf life of vaccines. And at the same time, cost is reduced, and it facilitates the large-scale promotion and application of vaccines in high-temperature areas and areas with insufficient cold storage equipment.

What is claimed is:

1. A heat-resistant H1N1 subtype influenza virus mutant strain rPR8-HA-N5, which has been preserved at the China Center for Type Culture Collection, Wuhan University, Wuhan, China with the preservation number of CCTCC No. V202043.

2. The influenza virus mutant strain rPR8-HA-N5 according to claim 1, wherein the influenza virus mutant strain rPR8-HA-N5 is obtained by using a H1N1 subtype influenza virus PR8-E strain as a parent strain, and introducing five amino acid mutations in an HA gene thereof with lysine at position 2 mutated to glutamic acid, arginine at position 91 mutated to serine, the lysine at position 158 mutated to alanine, the lysine at position 252 mutated to glutamic acid, and lysine at position 516 mutated to glutamic acid, so as to obtain the heat-resistant H1N1 subtype influenza virus mutant strain rPR8-HA-N5, an HA protein gene of the influenza virus mutant strain rPR8-HA-N5 has the sequence of SEQ ID NO: 1.

* * * * *